United States Patent [19]
Keiner

[11] 3,972,998
[45] Aug. 3, 1976

[54] HAIR PREPARATION CONTAINING A FLUOROPOLYMER

[75] Inventor: John Anthony Keiner, London, England

[73] Assignee: Lever Brothers Company, New York, N.Y.

[22] Filed: Nov. 15, 1974

[21] Appl. No.: 524,004

Related U.S. Application Data

[63] Continuation of Ser. No. 174,214, Aug. 23, 1971, abandoned, which is a continuation of Ser. No. 79,628, Oct. 9, 1970, abandoned.

[30] Foreign Application Priority Data

Oct. 24, 1969  United Kingdom............... 52301/69

[52] U.S. Cl................................. 424/70; 252/542; 252/544; 252/545; 252/546; 252/547; 252/549; 252/551; 252/554; 252/558; 424/DIG. 1; 424/DIG. 2; 424/47; 424/71; 424/78; 424/81
[51] Int. Cl.[2].......................................... A61K 7/06
[58] Field of Search.................. 424/DIG. 1, DIG. 2, 424/71, 47, 70, 78, 81; 260/89.5 H, 86.1 R, 86.1 N, 86.1 E; 252/542, 544, 545, 546, 547, 549, 551, 554, 558, DIG. 2, DIG. 3, DIG. 13

[56] References Cited
UNITED STATES PATENTS 3,459,696   8/1969   Read............................. 260/89.5 H

FOREIGN PATENTS OR APPLICATIONS 1,024,497   3/1966   United Kingdom............. 260/556 F
1,024,498   3/1966   United Kingdom............. 260/556 F
1,049,063   11/1966  United Kingdom............. 260/556 F Primary Examiner—Albert T. Meyers
Assistant Examiner—Vera C. Clarke
Attorney, Agent, or Firm—Arnold Grant

[57] ABSTRACT

A hair cosmetic composition, for example a shampoo, for the treatment of wet hair on the head to reduce the time necessary for drying the hair, including a vinyl polymer containing monomers of the general formula

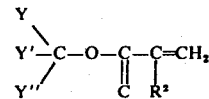

where Y is a partially or wholly fluorinated $C_1$–$C_{11}$ alkyl group and Y' and Y'' individually are either the same or different partially or wholly fluorinated $C_1$–$C_{11}$ alkyl groups or hydrogen atoms and $R^2$ is a hydrogen atom or a methyl group.

8 Claims, No Drawings

HAIR PREPARATION CONTAINING A FLUOROPOLYMER

This is a continuation, of application Ser. No. 174,214, filed Aug. 23, 1971, which is a continuation of application Ser. No. 79,628, filed Oct. 9, 1970; both now abandoned.

BACKGROUND OF THE INVENTION

1. Field of the Invention

This invention relates to the treatment of hair and more particularly relates to compositions for treating human hair and to methods of carrying out such treatment.

2. Description of the Prior Art

In many treatments applied to hair on the head, especially ladies' hair, the hair is made wet. The drying of the hair following such treatments is a time-consuming operation and may take up a high proportion of the treatment time. Copending application Ser. No. 819,449 describes how certain fluoropolymers have the effect of substantially reducing the drying time when they are applied to the hair. We have found, however, that this effect is not common to all fluoropolymers, nor even to those which endow the hair with water-repellent properties.

BRIEF SUMMARY OF INVENTION

It is an object of this invention to provide a further class of hair cosmetic compositions containing a fluoropolymer which will provide wet hair with quick drying properties.

According to the present invention there is provided a hair cosmetic preparation comprising a vinyl polymer derived from a fluorine-containing monomer of the general formula

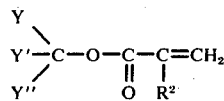

where Y is a partially or wholly fluorinated $C_1$–$C_{11}$ alkyl group and Y' and Y'' individually are either the same or different partially or wholly fluorinated $C_1$–$C_{11}$ alkyl groups or hydrogen atoms, and $R^2$ is a hydrogen atom or a methyl group.

It is preferred that the vinyl polymer is derived from a fluorine-containing monomer of the general formula

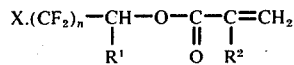

where X is a hydrogen or fluorine atom $R^1$ is a hydrogen atom or a $C_1$ to $C_{11}$ perfluoroalkyl group $R^2$ is a hydrogen atom or a methyl group, and $n$ is an integer from 1 to 11.

$R^1$ is preferably a hydrogen atom or a trifluoromethyl group, and $n$ is preferably an integer from 1 to 9.

These monomers are hereinafter referred to as "fluorinated monomers" and the polymers produced from these as "vinyl polymers".

By a hair cosmetic preparation is meant a preparation intended to be applied to the hair for cleansing, beautifying, promoting attractiveness or altering the appearance of the hair. Examples of hair cosmetic preparations are hair shampoo, waving, setting, bleaching, colouring, conditioning and hair dressing products, particularly those hair dressing products in the form of an aerosol spray of a solution or in the form of an aqueous latex emulsion.

The vinyl polymers employed in this invention are formed by vinyl polymerisation, i.e., free radical catalysed polymerization of terminally unsaturated monomers. The polymers employed can be homopolymers of the fluorinated monomers or copolymers of these monomers and monomers of other kinds which contain an ethylenic linkage, for example alkylenes, such as ethylene and propylene; halogenated alkylenes such as vinyl fluoride, vinyl chloride, and vinylidine fluoride and chloride; other vinyl monomers such as vinyl acetate, and acrylonitrile conjugated dienes, such as butadiene, chloroprene and isoprene; alkyl, aminoalkyl or vinyl esters of acrylic and alkacrylic acids such as methacrylic acid. There may also be terpolymers or quaterpolymers of the fluorinated monomers.

Examples of preferred fluorinated monomers from which the polymers employed in this invention may be produced are hexafluoroisopropyl methacrylate and 1H, 1H perfluorobutyl methacrylate. In general, for reasons of effectiveness, we prefer to use ω-fluoro monomers rather than ω-hydro ones, and we also prefer copolymers and terpolymers to homopolymers although homopolymers of ω-hydromonomers also perform well.

One particular form of the hair cosmetic preparation of the invention is that of a shampoo. The shampoo, which may be in liquid, paste or gel form, can contain the usual synthetic detergents in conventional amounts. Examples of anionic detergents that may be used are: soaps of higher fatty acids containing from 8 to 26 carbon atoms; long-chain primary or secondary alkyl sulphates containing from 8 to 22 carbon atoms, such as lauryl sulphate; esters of sulphuric acid and polyols partially esterified with higher fatty acids, for example the monosulphate of tallow monoglyceride; sulphated alkanolamides of higher fatty acids; alkyl ether sulphates, for example lauryl ether sulphate; hydroxysulphonated esters of higher fatty acids; esters of higher fatty acids and low molecular weight hydroxyalkane sulphonic acids, for example, the oleic ester of isethionic acid; amides of higher fatty acids and aminoalkane sulphonic acids, for example the oleic amide of taurine; water-soluble alkyl phosphates; sulphated reaction products of alkylene oxide with hydrophobic materials as described below; sulphonated oils; sulphonated higher fatty acids; primary and secondary alkyl sulphates; olefin sulphonates; and sulphonates of alkyl aromatic hydrocarbon compounds possessing an alkyl substituent containing from 8 to 26 carbon atoms (with a mono- or polynuclear structure).

Alkyl sulphates or alkyl ether sulphates are normally present in the compositions in an amount of at least about 6%, for example from about 8 to about 45%, by weight of the shampoo. Preferred detergent components of the shampoo are sodium, magnesium, ammonium, mono-, di-, and triethanolamine salts of sulphated fatty alcohols as well as the salt of sulphonated alkylaryl compounds all having alkyl groups containing from about 12 to about 21 carbon atoms. Further examples of specific typical anionic detergents which may be employed in the shampoo are sodium lauryl sulphate, monoethanolamine lauryl sulphate, sodium lauryl ether sulphate and sodium dodecylbenzene sulphonate.

Examples of typical cationic detergents are alkylamine salts; quaternary ammonium salts; and acylalkanolamine salts. Specific examples of these cationic detergents are cetyl trimethyl ammonium chloride, N-lauryl pyridinium chloride and such compounds as dodecyl trimethyl ammonium bromide. As non-ionic detergents that may be used in the compositions according to the present invention may be mentioned: condensation products of alkylene oxides with hydrophobic compounds such as higher fatty alcohols, for instance a condensation product of oleyl alcohol with 20 equivalents of ethylene oxide, polyols, for instance reaction products of propylene glycol and propylene oxide, alkyl phenols, for instance condensation products of nonyl phenol and ethylene oxide, products of the reaction of propylene oxide with ethylene diamine, fatty acid amides, amides of alkane sulphonic acids, and substituted polyamines. Other nonionic products are those such as the condensation products of fatty acid chlorides and hydrolyzed natural proteins, esters of higher fatty acids and sugars, for instance sorbitan monolaurate, and alkylolamides, for instance coconut monoethanolamide and oleic diethanolamide. Fatty amine oxides, for instance dimethylhexadecylamine oxide may also be used.

The ampholytic detergents that can be used are, for example, salts of N-alkylated compounds as $\beta$-aminopropionic acid, imidazolines, betaines and sultaines. Specific examples of such detergents which have been found to be suitable are the fatty $\beta$-alanines such as N-dodecyl-$\beta$-alanine, the partial sodium salt of N-lauryl-$\beta$-imino-dipropionate, and N-coco-$\beta$-amino-butyric acid. Other examples are N-dodecyl-N,N-dimethylamino-acetic acid, the inner salt of 2-trimethylaminolauric acid, the so-called fatty imidazolines such for example as the sodium salt of 1-(carboxymethyl)-1-(2-hydroxyethyl)-2-coco-imidazolinium hydroxide.

The amount of the vinyl polymer included in the hair cosmetic preparation may vary from 0.0001 to 5% or 6% by weight of the composition. Preferably, the amount of the polymer is from 0.0015 to 1% and a particularly preferred range is 0.0015 to 0.02% by weight.

Instead of being applied from a shampoo, the vinyl polymer may be applied to the hair separately from other hair cosmetics, for instance after shampooing. As mentioned above, the vinyl polymer can be applied (for example in the form of an aerosol spray) as a solution in a suitable innocuous organic solvent or as an aqueous latex emulsion. The vinyl polymer is suitable applied in this manner in the same concentrations as stated above in respect of shampoo compositions.

The hair cosmetic compositions of the invention may include the normal additives common to the art, for example perfumes, germicides, colorants, organic solvents, inorganic builders, foam improvers and stabilizers, preservatives, protein hydrolyzates, antioxidants and thickeners.

In another aspect, the invention relates to the treatment of wet hair on the head to reduce the time required for the drying thereof, which comprises applying to the wet hair the above vinyl polymer.

A typical sequence of steps in the performance of the invention when the vinyl polymer is applied during a shampooing treatment but not directly from shampoo itself is: shampoo the hair, towel dry, apply vinyl polymer, allow vinyl polymer to remain in contact with the hair for up to 10 minutes, rinse, dry.

The vinyl polymer is effective in reducing the drying time of wet hair even when applied from solutions of extremely low concentration. It is believed that effective and useful preparations containing vinyl polymer in such minor amounts are novel and accordingly, therefore, in a further aspect of the invention there is provided a lotion for applying to the hair to reduce the time required for the drying thereof when it is wet, which consists of an aqueous latex emulsion of the above vinyl polymer in a concentration of 0.0001 to 0.02% by weight.

DETAILED DESCRIPTION OF INVENTION

The vinyl polymers exemplified in the following examples and tables were prepared in an aqueous emulsion using N,N-dimethyloctadecylamine acetate as a surfactant and 2,2$^1$-azobisisobutyramidine dihydrochloride as an initiator. However the preparation can also be achieved in bulk, solution or dispersion, and other surfactants and initiators and, if desired, chain transfer agents and cross-linking agents may be used.

The general procedure used will be illustrated by the following description of the emulsion polymerisation of 1$\underline{H}$, 1$\underline{H}$-perfluorobutyl methacrylate.

Procedure

The apparatus consisted of a 50 ml flanged flask fitted with a reflux water condenser (with a nitrogen bypass), a gas inlet for nitrogen, a thermometer and a rubber septum cap to allow addition of monomer and initiator by syringe. The flask was clamped in an oil bath capable of maintaining temperature equilibrium to ±2°C.

Distilled water (30 g) and N,N-dimethyloctadecylammonium acetate (1.1 g) were refluxed in the flask for 1 hour while a current of nitrogen was passed through the apparatus. This procedure was judged as sufficient to purge the water and the apparatus of oxygen. The flow of nitrogen through the flask was then stopped, the flow of nitrogen through the bypass on the condenser was increased (to prevent entry of atmospheric oxygen into the apparatus), and the temperature of the flask was allowed to fall to 60°–65°C. Acetone (3 g) and then 1H, 1H-perfluorobutyl methacrylate (10 g) was added to the flask from a syringe. The stirring rate was kept constant at a speed sufficient to give a semi-stable suspension of monomer in water. The temperature was allowed to come to an equilibrium (62°C) and then an aqueous solution of $\alpha,\alpha'$-azobisisobutyramidine dihydrochloride (0.01 g ml$^{-1}$) (2.5 mls) was allowed to drip slowly into the rapidly stirred suspension. Over a period of 20 mins. the temperature was observed to rise to 65°C and the suspension became clear while simultaneously developing a bluish tint.

Stirring was maintained for 4 hours after the addition of the initiator and the mixture was then cooled and poured out of the flask.

The latex was quite easily coagulated by acetone and the resulting polymer was easily soluble in Arcton 113 ($CF_2Cl.CFCl_2$).

EXAMPLE 1

Switches of hair weighing 6 g were washed in a shampoo solution containing monoethanolamine lauryl sulphate (10%) and 0.003% or 0.3% by weight of the vinyl polymer solids. The solution was adjusted to pH7 by the addition of acid or alkali. The wet switches were towel dried and then kept in an enclosure were they were submitted to forced convection at 45°C. Each switch was weighed at various time intervals and the time taken for it to dry to constant weight was noted.

Similar data were obtained for a control switch which had been treated in an identical manner with a neutral shampoo solution containing 10% of monoethanolamine lauryl sulphate, but no vinyl polymer.

For purposes of comparison, the drying time of a shampoo containing 0.003% of the polymer solids of a commercially available fluoropolymer emulsion, Zepel B (Trade Mark) was also determined. Although this determination was performed at pH8 rather than pH7 as in the remainder of the examples, we consider that the drying time values are not significantly affected by this difference.

The drying time of the treated switches was expressed as a fraction (hereinafter called the drying time value) of the drying time of the control switch. The results for a shampoo containing 0.003% of the vinyl polymer are shown in Table 1.

TABLE 1

Drying time values for shampoos containing polymers which are:
a. homopolymers of fluorinated monomers
b. copolymers of fluorinated monomers and N,N-diethylamino methacrylate (DAM)
c. terpolymers of fluorinated monomers, N,N-diethylamino methacrylate and butyl methacrylate (BM)

| Polymer No. | Fluorinated Monomer (FM) | | | | Co-monomers | | Monomer Wt. Ration FM:DAM:BM | Drying Time Value |
|---|---|---|---|---|---|---|---|---|
| | X | n | R | $R^2$ | DAM | BM | | |
| 1 | F | 7 | H | H | ✓ | ✓ | 1:1:1 | 0.66 |
| 2 | F | 7 | H | H | ✓ | — | 1:1 | 0.66 |
| 3 | F | 7 | H | H | — | — | — | 0.80 |
| 4 | F | 7 | H | $CH_3$ | — | — | — | 0.90 |
| 5 | F | 7 | H | $CH_3$ | ✓ | — | 1:1 | 0.70 |
| 6 | F | 7 | H | $CH_3$ | ✓ | ✓ | 1:1:1 | 0.80 |
| 7 | F | 1 | $CF_3$ | $CH_3$ | — | — | — | 0.78 |
| 8 | F | 1 | $CF_3$ | $CH_3$ | ✓ | — | 1:1 | 0.67 |
| 9 | F | 3 | H | $CH_3$ | ✓ | — | 1:1 | 0.67 |
| 10 | H | 6 | H | H | — | — | — | 0.73 |
| 11 | H | 6 | H | H | ✓ | — | 1:1 | 0.88 |
| 12 | H | 6 | H | $CH_3$ | — | — | — | 0.90 |
| 13 | F | 1 | $CF_3$ | $CH_3$ | ✓ | ✓ | 1:1:1 | 0.80 |
| 14 | H | 8 | H | $CH_3$ | — | — | — | 0.90 |
| 15 | H | 6 | H | $CH_3$ | ✓ | — | 1:1 | 0.80 |
| 16 | H | 8 | H | H | ✓ | — | 1:1 | 0.90 |
| 17 | H | 8 | H | $CH_3$ | ✓ | — | 1:1 | 0.88 |
| 18 | H | 6 | H | H | ✓ | ✓ | 1:1:1 | 0.90 |
| 19 | H | 6 | H | $CH_3$ | ✓ | ✓ | 1:1:1 | 0.90 |
| 20 | H | 8 | H | $CH_3$ | ✓ | ✓ | 1:1:1 | 0.80 |
| 21 | Zepel "B" | | | | ✓ | ✓ | 1:1:1 | 1.00 |

The table shows the reduction in the time needed for drying a switch of hair which is achieved when a shampoo containing one of the fluoropolymers of the invention is used for washing the hair, compared with the time needed for drying the same switch after it has been washed with a shampoo containing no fluoropolymer. It also shows the reduction in the drying time produced by using a shampoo containing a fluoropolymer according to the invention compared with the drying time needed when the hair is washed with a shampoo containing Zepel B, a polymer which is capable of giving a water-repellency effect to hair.

Zepel B is cationic emulsion polymer containing fluorooctyl groups which is manufactured by E. I. du Pont de Nemours & Co.

What is claimed is:

1. A method for reducing the time required for drying hair on the head, which comprises applying thereto an effective amount of hair cosmetic preparation containing from about 0.001 to about 6% by weight of a vinyl polymer of a fluorine-containing monomer of the formula:

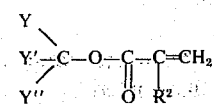

where Y is selected from the group consisting of a partially and wholly fluorinated $C_1-C_{11}$ alkyl group and Y' and Y'' individually are selected from the group consisting of partially and wholly fluorinated $C_1-C_{11}$ alkyl groups and hydrogen and $R^2$ is selected from the group consisting of hydrogen and methyl and a cosmetically acceptable carrier thereof.

2. The method according to claim 1 wherein the fluorine-containing monomer is of the formula

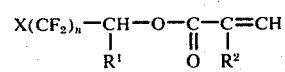

where X is selected from the group consisting of hydrogen and fluorine, $R^1$ is selected from the group consisting of hydrogen and $C_1$ to $C_{11}$ perfluoroalkyl group, $R^2$ is selected from the group consisting of hydrogen and methyl, n is an integer from 1 through 11.

3. The method according to claim 2 wherein $R^1$ is selected from the group consisting of hydrogen and trifluoromethyl.

4. The method according to claim 2 wherein n is an integer from 1 through 9.

5. The method according to claim 1 wherein the hair cosmetic preparation is a shampoo.

6. The method according to claim 1 wherein the vinyl polymer comprises a fluorine-containing monomer selected from the group consisting of hexafluoroisopropyl methacrylate, and 1$\underline{H}$, 1$\underline{H}$ perfluorobutyl methacrylate.

7. A shampoo containing from about 0.001 to about 6% by weight of a copolymer of (1) a fluorine-containing monomer of the formula:

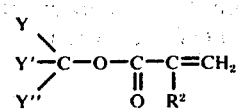

where Y is selected from the group consisting of a partially and wholly fluorinated $C_1$–$C_{11}$ alkyl group and Y' and Y'' individually are selected from the group consisting of partially and wholly fluorinated $C_1$–$C_{11}$ alkyl groups and hydrogen and $R^2$ is selected from the group consisting of hydrogen and methyl and (2) a monomer selected from the group consisting of N-N-diethylamino methacrylate, butyl methacrylate and mixtures thereof, and a cleansing effective amount of a detergent.

8. A hair shampoo containing from about 0.001 to about 6% of a copolymer comprising (1) a fluorine-containing monomer selected from the group consisting of hexafluoroisopropyl methacrylate and 1$\underline{H}$, 1$\underline{H}$ perfluorobutyl methacrylate and (2) a monomer selected from the group consisting of N,N-diethylamino ethyl methacrylate, and butyl methacrylate, and a cleansing effective amount of a detergent.

* * * * *